United States Patent [19]

Barlow

[11] Patent Number: 5,053,002
[45] Date of Patent: Oct. 1, 1991

[54] IRRIGATION SYSTEM FOR ANGIOSCOPE

[75] Inventor: David E. Barlow, Hicksville, N.Y.

[73] Assignee: Olympus Corporation, Lake Success, N.Y.

[21] Appl. No.: 405,046

[22] Filed: Sep. 7, 1989

Related U.S. Application Data

[63] Continuation of Ser. No. 141,936, Jan. 11, 1988, abandoned.

[51] Int. Cl.[5] .............................................. A61M 1/00
[52] U.S. Cl. ................................... 604/30; 604/153; 604/245
[58] Field of Search ................... 604/30, 67, 131, 140, 604/151, 153, 181, 182, 245

[56] References Cited

U.S. PATENT DOCUMENTS

| | | | |
|---|---|---|---|
| 3,701,345 | 10/1972 | Heilman et al. | 604/67 |
| 4,006,736 | 2/1977 | Kranys et al. | 604/67 |
| 4,337,770 | 7/1982 | Young et al. | 604/30 |
| 4,367,736 | 1/1983 | Gupton | 604/30 |
| 4,372,304 | 2/1983 | Avakian et al. | 604/30 |
| 4,529,397 | 7/1985 | Hennemuth et al. | 604/30 |
| 4,553,958 | 11/1985 | Le Cocq | 604/67 |
| 4,650,462 | 3/1987 | DeSatnick et al. | 604/30 |
| 4,655,197 | 4/1987 | Atkinson | 604/30 |
| 4,670,006 | 6/1987 | Sinnett et al. | 604/67 |
| 4,756,706 | 7/1988 | Kerns | 604/67 |

*Primary Examiner*—C. Fred Rosenbaum
*Assistant Examiner*—Anthony Gutowski
*Attorney, Agent, or Firm*—Kenyon & Kenyon

[57] ABSTRACT

An angioscope has irrigation system with at least two presettable irrigant flow rates. A footswitch under manual control is operatively connected to a roller pump for switching from a high first flow rate to a low second flow rate. Upon an initial filling of a blood vessel under observation with clear irrigant at the high flow rate, the operator switches to the low flow rate. The rate of fluid flow may alternatively be continuously variable under manual control.

8 Claims, 7 Drawing Sheets

FIG. 1

PRIOR ART

IRRIGATION SYSTEM FOR ANGIOSCOPE

This application is a continuation, of application Ser. No. 07/141,936, filed Jan. 11, 1988, which is now abandoned.

BACKGROUND OF THE INVENTION

The present invention relates to an irrigation system usable with an angioscope.

The angioscope is a medical instrument for viewing inside the cardiovascular system. The most common application of angioscopy is to view the interior lumen of veins and arteries, although angioscopes have also been used to inspect the interior of the heart and other organs. The size of the vessels which can be inspected by angioscopy is limited by the outer diameter of the insertion portion of the angioscope. Vessels ranging from small coronary arteries to large peripheral vessels may all be inspected by the appropriate instrument.

An angioscope generally comprises an insertion portion in the form of a tube traversed in the longitudinal direction by an optical guide for transmitting light energy from an external source into the interior lumen of a blood vessel into which the insertion portion of the angioscope has been inserted. The insertion tube also carries an optical guide for transmitting light energy from a lens at the distal end of the insertion tube to an eyepiece or a video system for enabling observation of images from inside the blood vessel.

In order to obtain a visual image of an inner surface of a blood vessel, the blood within the vessel must be displaced. Generally, blood displacement is accomplished via the introduction of a clear fluid into the blood vessel in a region about the distal tip of the angioscope. Conventional irrigation systems require the full attention of an assistant of the endoscopist performing the angioscopy procedure. The assistant controls, under the supervision of the endoscopist, the pressure and flow rate of the clear fluid into the blood vessel under observation.

An object of the present invention is to provide, for use with an angioscope, an irrigation system which eliminates the need for the full attention of an assistant and, once the system is set up, can be operated under the complete control of an endoscopist performing an angioscopy procedure.

Another object of the present invention is to provide such an angioscope irrigation system wherein the amount of an irrigant infused into a patient is easily minimized.

Another, more particular, object of the present invention is to provide such an angioscope irrigation system wherein the flow rate of irrigant during an infusion operation can be precisely selected or preselected.

Another particular object of the present invention is to provide such an angioscope irrigation system wherein the operator is continuously provided with an indication of both the current flow rate and the total volume of irrigant infused.

SUMMARY OF THE INVENTION

An irrigation system for use with an angioscope comprises, in accordance with the present invention, a fluid infusion component such as a tube or a catheter, a source of substantially transparent irrigation fluid, a conduit establishing a flow path from the fluid source to the infusion tube, and a drive in contact with the conduit for moving fluid from the fluid source through the conduit and through the infusion tube. The fluid drive has a plurality of modes of operation for moving fluid through the conduit at a plurality of different flow rates. A control device is operatively connected to the fluid drive and includes a manually actuable control for selecting a first mode of operation of the fluid drive and a concomitant first rate of fluid flow through the conduit, for selecting a second mode of operation of the fluid drive and a concomitant second rate of fluid flow through the conduit, and for shifting the fluid drive from the first mode to the second mode in response to actuation of the control by an operator. Pursuant to the invention, an operator can selectively induce a desired change in the rate of fluid flow through the conduit and through the infusion tube upon observing, e.g., via an optical guide of an angioscope, a given condition in a blood vessel into which the distal end of the infusion tube has been inserted.

Pursuant to a preferred feature of the present invention, at least one manually actuatable selector is provided for presetting the modes of operation of the fluid drive so that each of the different flow rates has a respective predetermined value.

Pursuant to particular features of the present invention, the conduit includes a flexible hose and the fluid drive takes the form of a roller pump in contact with the hose. Moreover, a sensor is advantageously provided for automatically detecting an air bubble in fluid being moved through the conduit and for automatically deactivating the fluid drive upon detection of an air bubble. To that end, the conduit may include a bubble chamber portion juxtaposable to the bubble sensor. The conduit may also include a pressure chamber juxtaposable to another sensor designed to monitor fluid pressure in the conduit.

Pursuant to yet further features of the present invention, displays are provided for indicating a total amount of fluid pumped through the conduit during an injection or infusion operation, and a rate of fluid flow through the conduit.

An angioscope irrigation system in accordance with the present invention enables an operator to preset a high first flow rate and a low second flow rate and to automatically switch from the high flow rate to the low flow rate upon detecting that a blood vessel under observation has been cleared of blood. The low rate of irrigant flow is high enough to maintain the blood vessel portion under observation free of blood and yet minimizes the total amount of irrigant infused into the patient. Other features and advantages of the present invention will be readily apparent from the following detailed description.

DETAILED DESCRIPTION

Figure 1:
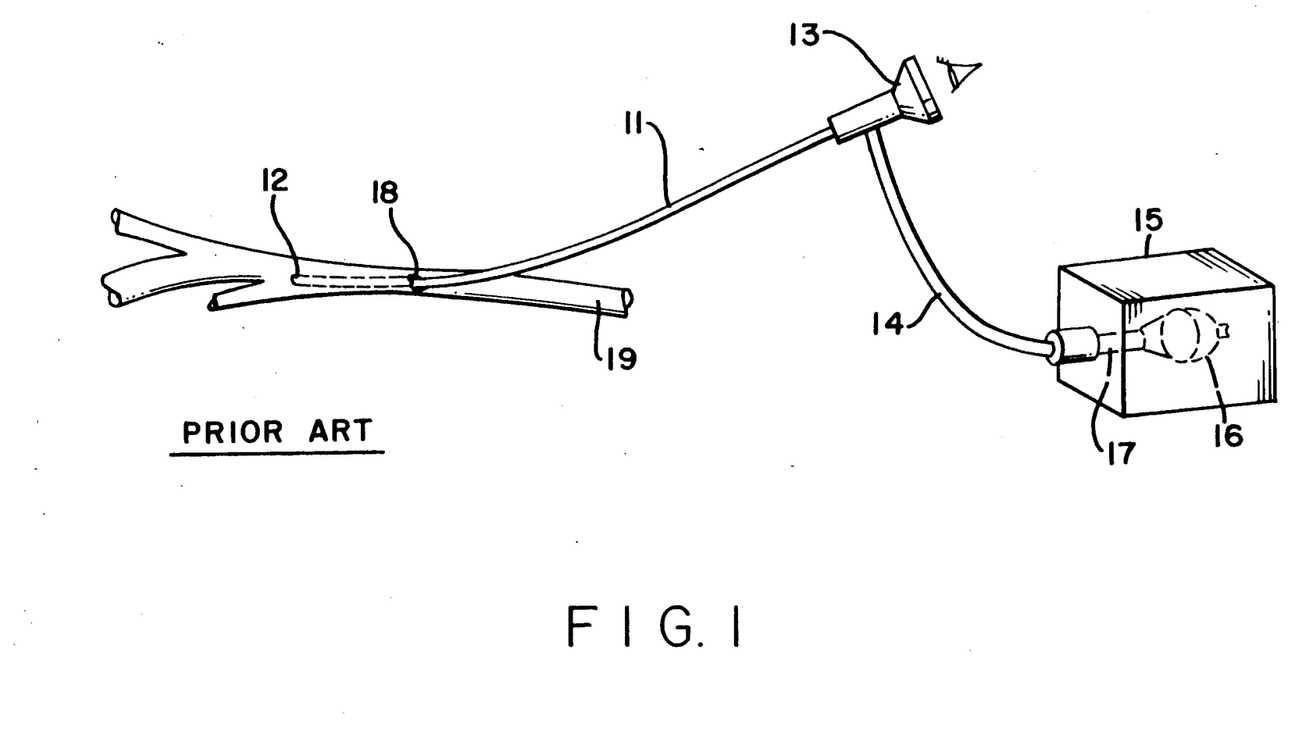
FIG. 1 is a schematic isometric view of a conventional angioscope for viewing the interior lumen of a blood vessel.

As shown in FIG. 1, an angioscope typically includes a flexible or rigid insertion portion 11 which is inserted through an incision 18 in a blood vessel 19 to be examined. A distal tip 12 of the instrument contains an objective lens (not illustrated) for focusing an image of the vessel interior at an input focal plane of an image transmission system contained within the insertion portion of the instrument. A fiberoptic or relay lens system (not illustrated) transfers the image to an eyepiece 13 which allows the operator to view the interior of the blood vessel immediately surrounding the distal tip 12 of the instrument. By advancing insertion portion 11 of the angioscope into blood vessel 19 while simultaneously looking through eyepiece 13, the operator can thoroughly inspect the interior walls of the vessel. The angioscope is connected to an external light source 15 by means of a flexible connecting portion 14. The output illumination of the lamp 16 contained within light source 15 is focused on an end 17 of connecting portion 14. A fiberoptic bundle (not shown) running the entire length of the instrument carries the light from the input end of connecting portion 14 to distal tip 12 of insertion portion 11 for illuminating the interior of vessel 19.

Figure 2:
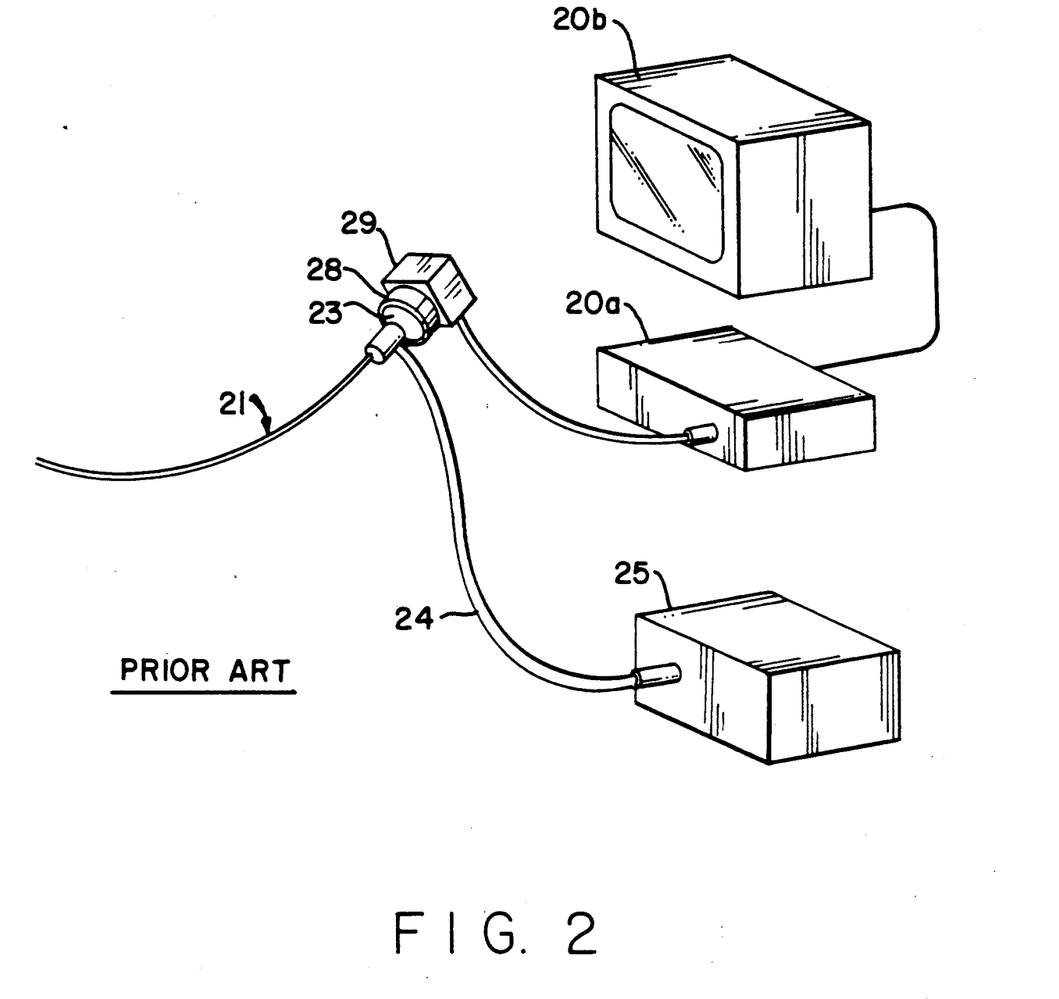
FIG. 2 is a schematic isometric view of another conventional angioscope system including a television camera and a TV monitor.

It is common practice to couple a video system to the eyepiece of an angioscope in lieu of looking through an eyepiece. FIG. 2 illustrates a video camera 29 attached to an eyepiece 23 of an angioscope 21 by means of a coupler 28. Light enters the system from a light source 25 via a connecting tube 24. A video signal generated by camera 29 is processed by a camera control unit 20a and a resulting angioscope image is displayed on a monitor 20b for viewing. The advantages of observing the image via the monitor include: allowing multiple personnel to observe or record the procedure simultaneously; freeing the physician's hands from holding the instrument to his eye; and aiding in maintaining a sterile operating environment by eliminating eye contact with the instrument.

A vessel under inspection will be normally filled with blood, which being opaque obscures the visual field. Therefore, for angioscopy to be successful, the lumen of the vessel must be cleared of blood at least within a region surrounding the imaging means disposed in distal tip 12 (FIG. 1) of the angioscope. A common method for clearing the blood is to introduce a clear physiologic saline or crystalloid cardioplegic solution into the blood vessel to displace the opaque blood and replace it with transparent solution through which the observer can see the vessel wall.

Figure 3:
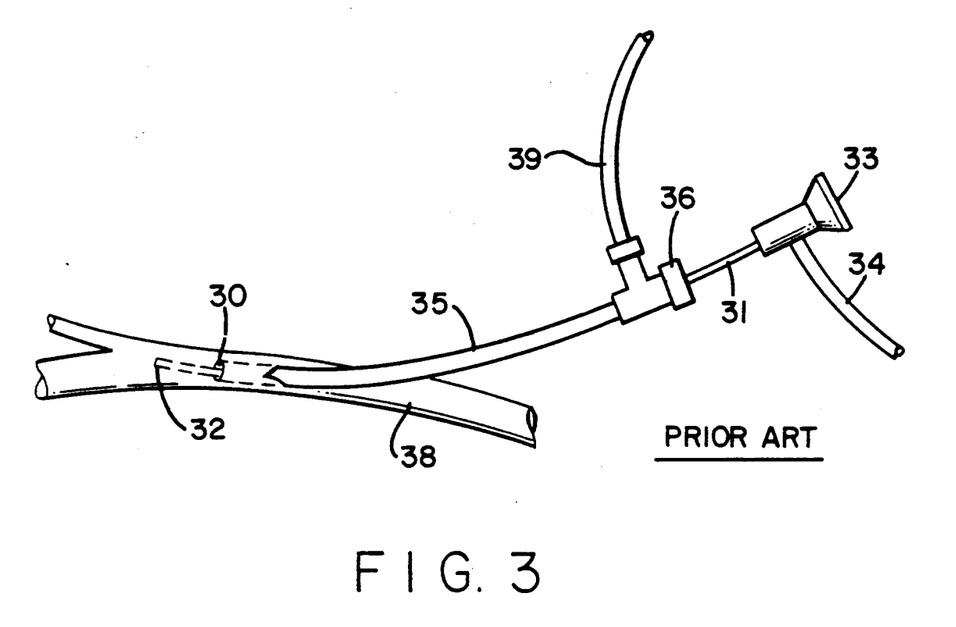
FIG. 3 is a schematic elevational view of an angioscope with a tube for the introduction of clear irrigant fluid.

One means of introducing transparent fluid into a blood vessel under examination is illustrated in FIG. 3. The insertion portion 31 of an angioscope is inserted through a catheter 35 into blood vessel 38. The catheter and the insertion portion of the angioscope can be advanced either independently or simultaneously as a single unit into the blood vessel under inspection. The length of the angioscope insertion portion which protrudes from the distal end of the catheter is adjustable and may be changed at the operator's discretion. In addition, catheter 35 may have a balloon cuff (not shown) at the tip to occlude the flow of the blood through the vessel.

Clear irrigant is introduced into catheter 35 through a supply tube 39. The irrigant flows through a substantially cylindrical space between an outer surface of angioscope insertion portion 31 and an inner wall or surface of catheter 35. The irrigant exits at a distal end 30 of catheter 35, filling the lumen of vessel 38 and displacing the blood which surrounds a distal tip 32 of the angioscope's insertion portion. A seal 36 at the proximal end of catheter 35 prevents irrigant from leaking out between the proximal end of the catheter and angioscope insertion portion 31. For enabling the viewing of the vessel interior, a fiberoptic light guide (not depicted) extends through a connecting tube 34 and insertion portion 31. Another optical guide (not shown) extends from insertion portion tip 32 to an eyepiece 33.

Figure 4:
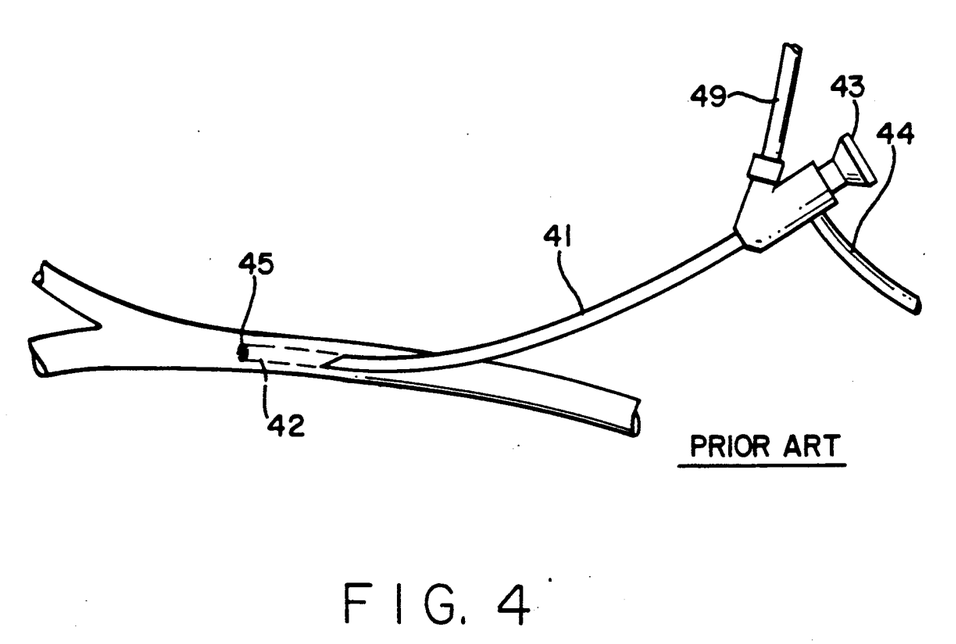
FIG. 4 is a schematic elevational view of an angioscope and an associated irrigation system.

FIG. 4 illustrates an alternate means of introducing irrigant into a blood vessel. In this design, an insertion portion 41 of an angioscope contains an internal channel (not illustrated) through which irrigant flows. Irrigant introduced through a supply tube 49 flows through the internal channel and exits from an orifice 45 at the distal tip 42 of the instrument. The insertion portion also contains an input light guide extending from a connecting tube 44 and an output light guide extending to an eyepiece 43. An advantage of the design of FIG. 4 is the increased ease of handling due to the absence of an independent external catheter. A disadvantage of the design of FIG. 4 is that the incorporation of an internal channel increases the diameter of the insertion portion of the instrument.

Figure 8:
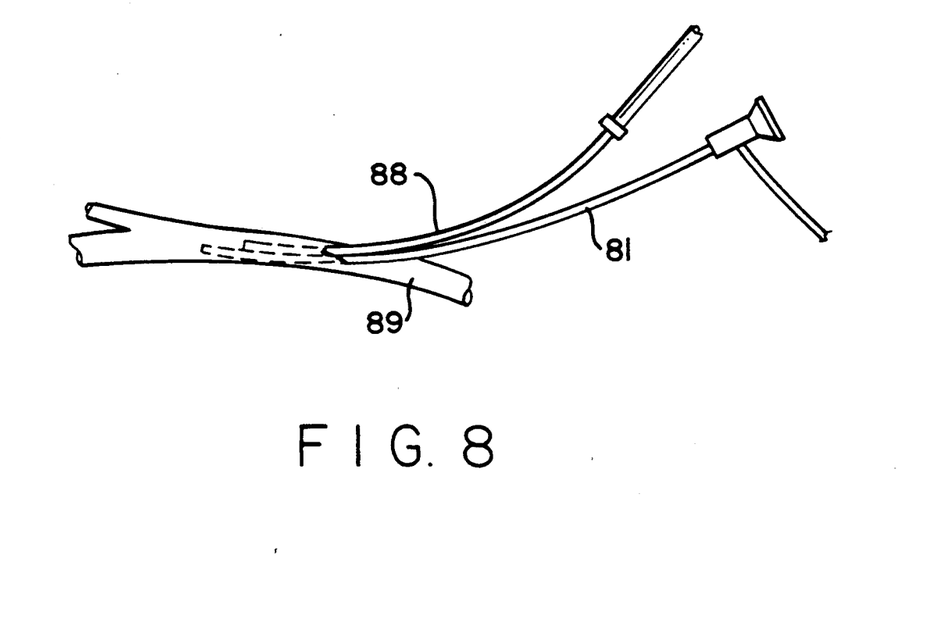
FIG. 8 is a schematic elevational view showing an angioscope together with a separate catheter for the introduction of irrigant into a blood vessel.
Figure 9:
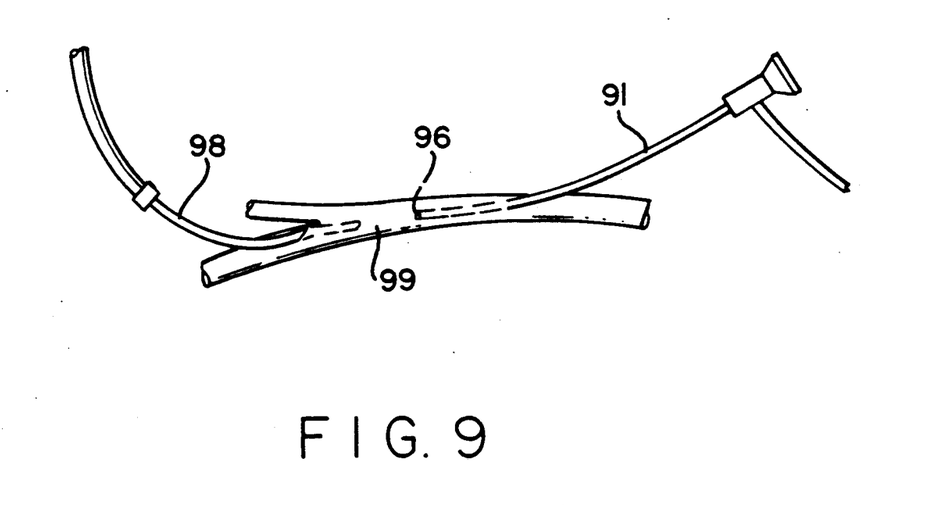
FIG. 9 is a schematic elevational view of an angioscope and a separate catheter, with different points of insertion into a blood vessel.

A conventional modification of the above-described designs, illustrated in FIG. 8, includes the introduction of the irrigant through a tube 88 inserted into a blood vessel 89 alongside an insertion portion 81 of the instrument. Tube or catheter 88 may be inserted through the same opening (FIG. 8) into vessel 89 or through a separate opening (FIG. 9). As depicted in FIG. 9, an irrigation catheter 98 may be inserted into a blood vessel 99 at a location upstream or downstream of a distal tip 96 of an endoscope 91. Other variations on the method of irrigation may include the use of multiple catheters or a combination of simultaneous irrigation through a catheter together with irrigation through an internal channel in the endoscope. Furthermore, both the irrigant inflow tube and the catheter 35 may have various lengths in relation to the insertion portion of the angioscope.

For angioscopy to be successful, two conditions must be met during introduction of the irrigant. First, the irrigant must be infused under sufficient pressure to overcome the pre-existing intra-lumenal blood pressure, thereby enabling a flow of clear irrigant from the fluid source, past the distal tip and the objective lens of the angioscope, out into the arterio-venous tree. Insufficient pressure will either fail to completely displace the blood initially or allow back bleeding of blood from side branches into the main vessel. Second, the irrigant must have a sufficient flow rate to replace irrigant which continually flows away from the vessel under examination into the arterio-venous tree. Because in many cases the angioscope is used to inspect vessels which are not isolated from other vessels, either by removal or clamping, the irrigant supplied readily flows into connecting side branch vessels, out of the distal or the proximal portion of the vessel under inspection, or from the vessel at the point of insertion of the angioscope due to an insufficient seal between the angioscope and vessel. Regardless of the cause of drainage of irrigant away from the site of observation, the lost irrigant must be replaced to prevent blood from returning to the observation site as the angioscopic procedure progresses. Thus, in all cases where fluid is lost owing to one or more of the aforementioned conditions, the irrigant must be replaced continuously throughout the period of observation.

It is clear that the pressure at which the irrigant is supplied and its flow rate are dependent upon one another. In fact, if all of the fluid flow resistances and systemic pressures are known, one factor can be calculated from the other. In the clinical setting, the operator generally directs his thinking to the flow rate and whether it is sufficient to keep the field clear of blood. The endoscopist is not usually concerned with pressure except to remain cautious regarding the danger of over-pressurizing and over-distending the vessel under observation.

Figure 5:
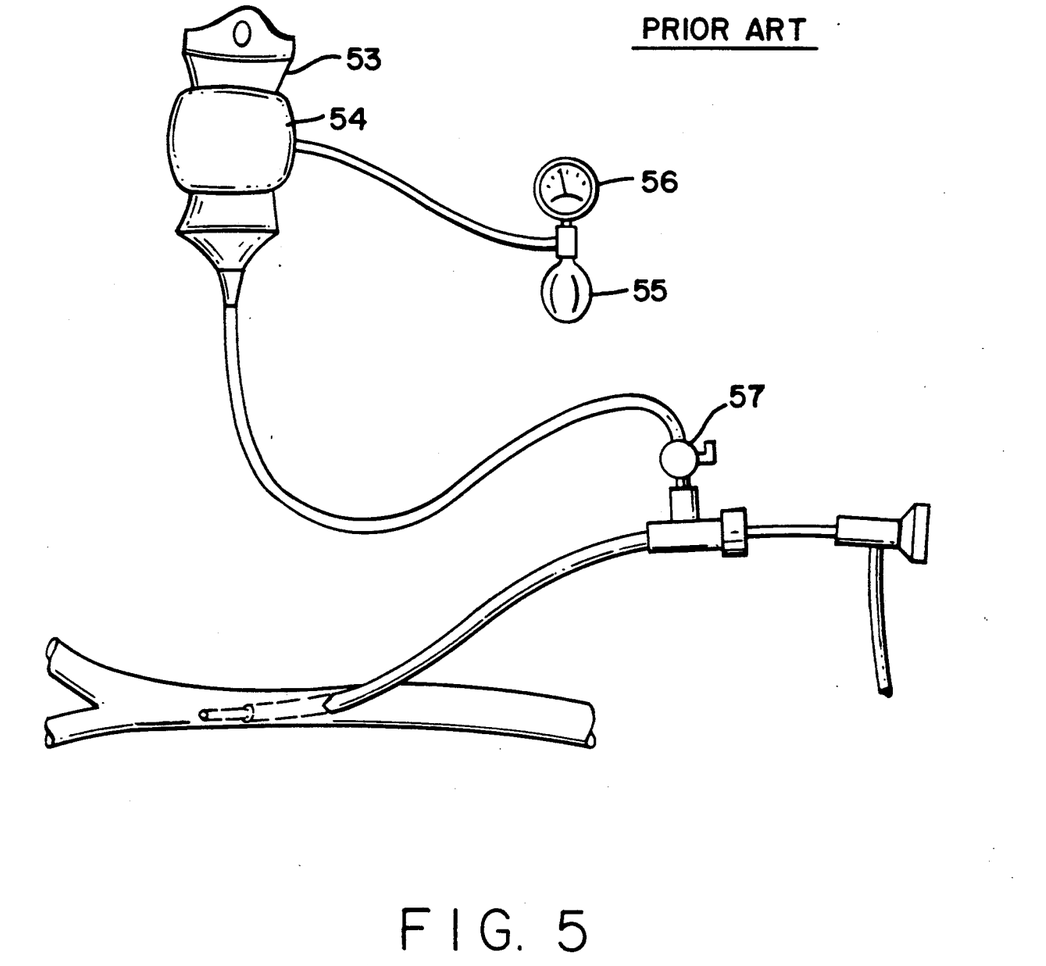
FIG. 5 is a schematic elevational view of an angioscope and an irrigation system including a fluid source surrounded by a pressurizable cuff.

FIG. 5 illustrates a common means of irrigating during angioscopy. A supply of clear irrigant is contained in a compressible bag 53 suspended near the patient. A pressure cuff 54 is wrapped around the bag to pressurize the irrigation system. The pressure in the cuff, and therefore the pressure in bag 53, is increased by squeezing a hand bulb 55 operatively coupled to the cuff. An operator can monitor the pressure by means of an attached pressure gauge 56, while a manually operated valve 57 is employed to stop and start the flow of irrigant as desired.

The irrigation system depicted in FIG. 5 has many problems when used in a clinical setting: (1) As fluid is drained from bag 53, the bag will lose pressure. A technical assistant is required to continuously monitor the pressure and intermittently pump up pressure cuff 54 as needed. To manage the irrigation system therefore requires the nearly full attention of an additional staff person. (2) Should the operator desire to irrigate at either a decreased or increased flow rate he must so inform the assistant who will then manually adjust the pressure in the cuff. This procedure is time consuming and awkward. (3) To start or stop the flow of irrigant, the operator must remove his hands from the surgical site and manually turn a valve, or so instruct his assistant. This procedure also is awkward and time consuming. (4) When the bag is drained, the assistant must deflate and remove the cuff, exchange the bag with a full one, or have an identical set-up at hand and change the supply tube to the backup system. These procedures are also awkward and time consuming. (5) The operator has no way of knowing the volume of irrigant he has infused into the patient during the procedure. (6) Due to the awkwardness of starting and stopping the flow of irrigant, as well as the difficulty in accurately controlling flow rate, it is typical for the operator to use a higher flow rate than is necessary and to have the irrigant flowing when it is not absolutely required. As a result, more fluid is used than is necessary. The excess irrigant compromises the health and safety of the patient.

Figure 6:
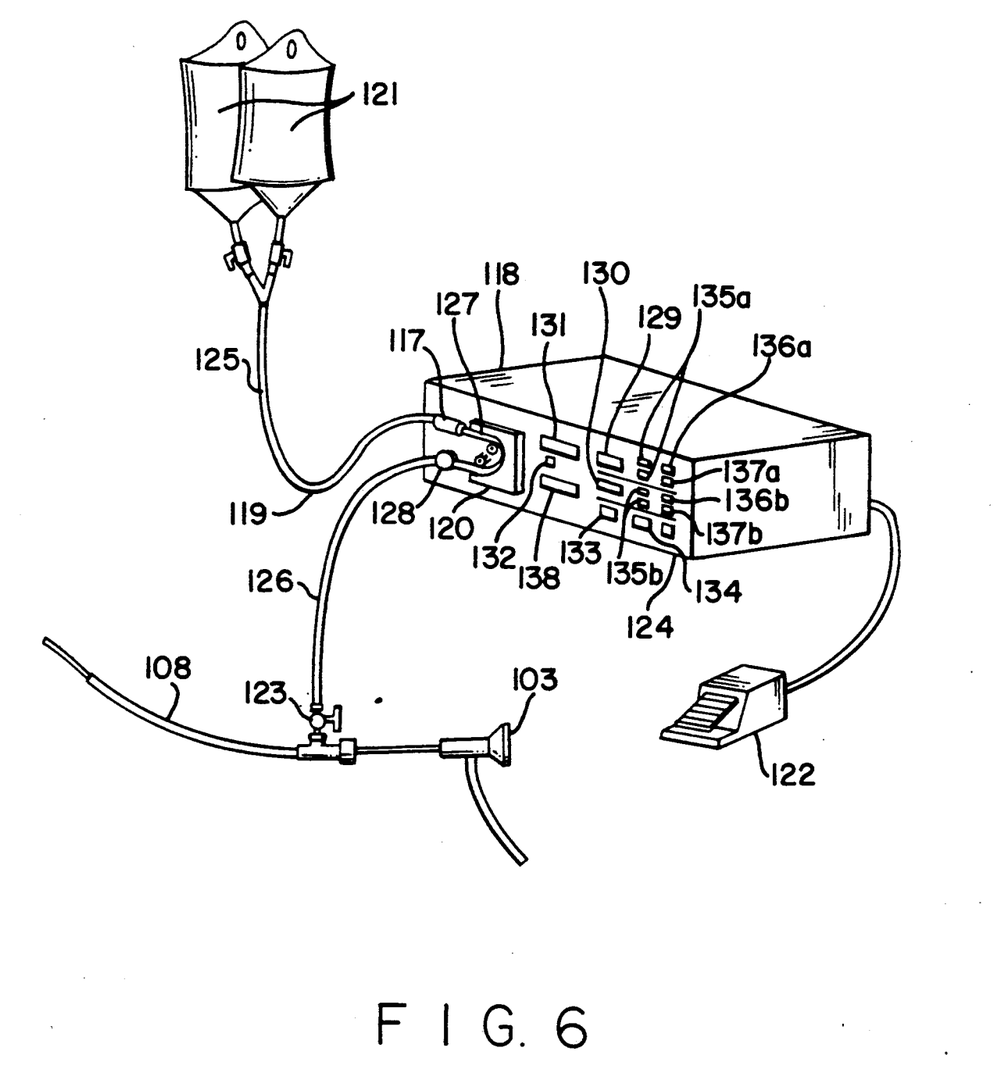
FIG. 6 is a partially schematic isometric view of an angioscope and an irrigation system in accordance with the present invention.

As shown in FIG. 6, an angioscope with an automated irrigation system comprises, in accordance with the present invention, a source 121 of irrigant solution, a calibrated pump unit 118, a control footswitch 122 and a tubing set 119. The source of irrigant solution typically takes the form of a plastic bag of sterile physiologic saline. Although a custom container for irrigant could be devised and attached to the pump, bags or bottles of sterile saline are readily available in a hospital environment and are convenient to use. As illustrated in FIG. 6, two or more bags may be coupled together to increase the volume of source 121.

Pump unit 118 houses a motor (not shown) coupled to a pump head 120. A roller pump is preferable insofar as contact between the sterile irrigant and non-sterile components of the pump is thereby avoided. The operator activates the pump by means of footswitch 122. Footswitch 122 provides the operator with direct control over starting and stopping the flow or irrigant.

Irrigant is pumped from the bags of saline source 121 through tubing set 119 which is advantageously single-use, sterile and disposable. The tubing set includes an inflow tube 125, an air bubble detection chamber 117, a pump head tube 127, a pressure chamber 128 and an outflow tube 126. The outflow tube is connected to a standard irrigation catheter 108 via a manual valve or stopcock 123 at a distal end of tubing set 119. Valve 123 prevents leakage of fluid while the system is being assembled and is not used during the angiographic procedure to start and stop irrigant flow because that function is performed by footswitch 122.

Air bubble detection chamber 117 fits into a holder (not depicted) on a front panel 124 of pump unit 118. Photodiodes (not shown) built into the holder measure light transmission through the walls of chamber 117 and the irrigant contained therein. A circuit in pump unit 118 monitors a light transmission signal generated by the photodiodes and automatically shuts off the pump if an air bubble is detected in chamber 117. This safety device prevents the pumping of air into a patient should the supply of irrigant run out or should bubbles develop in the inflow tube.

Pressure chamber 128 likewise fits into a holder (not illustrated) on front panel 124. A flexible diaphragm (not illustrated) on the back of the pressure chamber couples the pump head outflow pressure to an electronic transducer built into the pressure chamber holder. The detected outflow pressure is indicated on a display 138 on front panel 124 and is monitored by a safety circuit (not shown) which shuts off the pump should the pressure exceed a preset threshold.

Pump unit 11B has two independently adjustable modes of operation. The first mode produces a high pressure and flow rate for the purpose of initially filling a blood vessel rapidly with irrigant, thereby quickly displacing the blood in the vessel with a bolus of transparent fluid to clear the visual field in a minimum of time. If the operator were to stop the pump after infusing the initial bolus of fluid, the irrigant would gradually diffuse into side-branch vessels, the open lumens of the vessel under inspection and other outlets. Upon loss of the clear fluid, the pressure in the vessel under inspection would gradually decrease. Upon a drop in pressure below the surrounding arteriovenous pressures, blood would once again enter the vessel under inspection, obscuring the visual field.

If, on the contrary, the operator were to continue to pump at the rapid rate of the bolus infusion, he would easily maintain a clear visual field. However, an unnecessarily large quantity of fluid is then infused into the patient. Therefore, the pump pursuant to the present invention has an alternate, lower speed of operation for infusing irrigant at a rate just sufficient to keep the visual field clear and significantly lower than the rate used for the initial filling of the vessel. Due to the necessity of inspecting vessels of a variety of sizes ranging from small coronary arteries to large peripheral vessels, together with the inspection of vessels with a wide range of drainage characteristics, the flow rates in each of the two modes of operation are independently adjustable.

To activate the pump, footswitch 122 can be depressed preferably to two separate and distinct positions. Slight pressure causing slight depression of the footswitch activates the pump in the lower flow rate mode. Firm pressure with full depression of the pedal activates the pump in the higher flow rate mode. The actual flow rates in each mode are independently adjustable by controls on front panel 124.

Alternative designs of the footswitch are possible. For example, the footswitch may include two independent pedals, each pedal activating a different mode of operation. Another design employs a single, continuously variable footpedal which operates like an automobile accelerator, gradually increasing the flow rate as the pedal is increasingly depressed. Disadvantages of these two alternative designs include the possibility of confusing the operator with multiple pedals, and the operator's difficulty in precisely controlling a continuously variable pedal.

The amount of fluid infused with each revolution of pump head 120 is easily calculated. A microprocessor (not shown) contained within pump unit 118 for controlling pump speed is able to calculate the flow rate of fluid through the pump at all times. The preset flow rate for the high and low modes of operation are indicated on the front panel displays 129 and 130. Thus, the operator knows before activating footswitch 122 at what flow rate he will begin infusing fluid into the patient. The microprocessor also calculates the total amount of fluid infused and indicates this cumulative volume on a display 131 on front panel 124. A reset button 132 allows the operator to reset the cumulative volume display to zero.

A button 133 is provided on front panel 124 to override the air bubble detection system for initially priming the pump. During operation, should the bubble detection system detect a bubble in inflow tubing 125, the pump immediately stops and an indicator 134 on the front panel warns the operator of the condition.

The front panel also contains buttons 135a and 135b for increasing or decreasing the preset flow rates of each mode of operation, buttons 136a and 136b for manually activating the pump from the front panel in lieu of the footswitch, and buttons 137a and 137b for activating and deactivating the footswitch.

In a preferred embodiment of the present invention, bubble detection chamber 117 is not necessary inasmuch as the bubble detecting photodiodes are capable of sensing the presence of bubbles directly through the wall of the inflow tubing. Pressure chamber 128 and pressure display 138, as well as the associated electronic transducer (not illustrated) and pressure chamber holder (not illustrated), can also be eliminated insofar as knowledge of the pressure at the pump head does not give direct knowledge of the pressure delivered to a blood vessel under observation and the operator may not desire knowledge of pump head pressure. In addition, a special button for priming the pump is unnecessary if a bubble detector is not built into the pump.

A basic irrigation system in accordance with the present invention need include only irrigant source 121, tubing set 119, a variable speed pump preferably with a display of the rate at which irrigant is being pumped, and footswitch or actuator 122 for implementing variable control of the irrigant flow rate. With a variable speed pump and a continuously adjustable footswitch, pump speed is correlated with footswitch position so that the operator can depress the footswitch at or about a completely depressed position to produce a rapid or bolus-type infusion to clear the visual field. Thereupon the operator eases the pressure on the footswitch to slow the pump to a lower flow rate to keep the visual field cleared while simultaneously infusing a minimum amount of fluid. The variable speed footswitch accomplishes the function of the flow rate pre-selection buttons 135a and 135b, inasmuch as pump speed and flow rate are under the immediate and complete control of the operator.

In yet another variation of the embodiment illustrated in FIG. 6, buttons 135a and 135b are used for preselecting a high flow rate, while a low flow rate is controlled by an operator via footswitch 122 to fine tune the low flow rate to the minimum amount needed for maintaining a clear visual field upon the injection of a bolus of irrigant at the pre-selected high flow rate. Irrigant is injected from source 121 at the pre-selected high flow rate upon the depression of footswitch 122 to a lowermost position. In this embodiment of the present invention, inasmuch as the operator is able to fine tune the low flow rate by adjusting the degree of depression of the footswitch, non-sterile buttons on front panel 124 of pump unit 118 need not be touched.

In yet another embodiment of the present invention, front panel 124 is provided with a button or buttons (not illustrated) for preselecting a quantity of fluid to be pumped as a "bolus." Footswitch 122 would allow the operator to switch between a first mode of operation in which a high flow bolus of a preselected quantity of fluid is infused and a second mode of operation which produces a selectable lower continuous flow. During examination of a blood vessel, an operator switches between these two modes of operation by using foot switch 122.

In addition, it is to be noted that other features of the embodiment of FIG. 6 are not necessary for practicing the instant invention. In particular, footswitch activation and deactivation buttons 137a and 137b need not be provided, in which case footswitch 122 is continuously active.

Figure 7A:
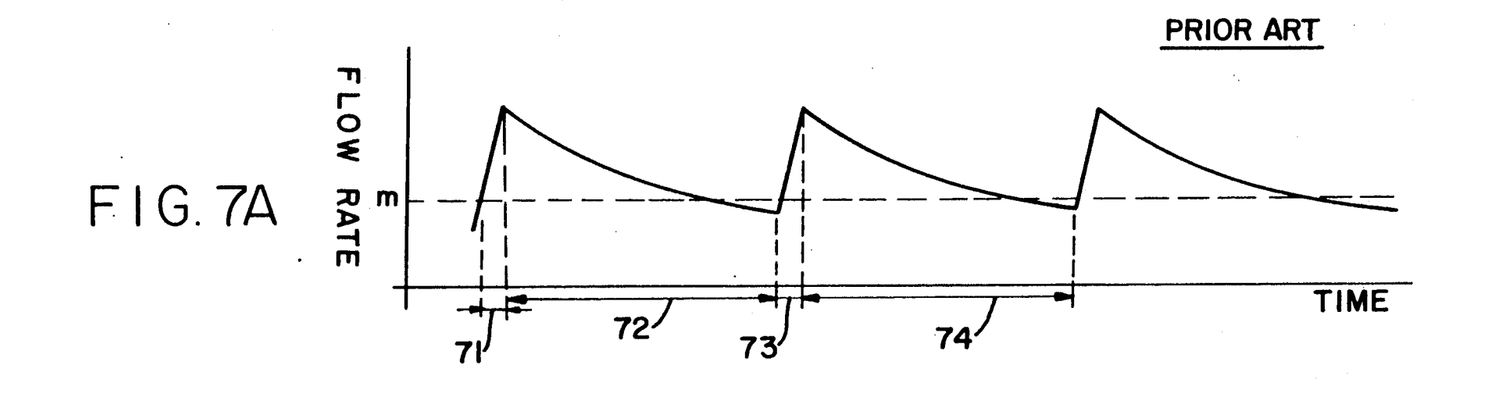
FIG. 7A is a graph of flow rate of an infused irrigant versus time in the conventional angioscope system of FIG. 5.
Figure 7B:
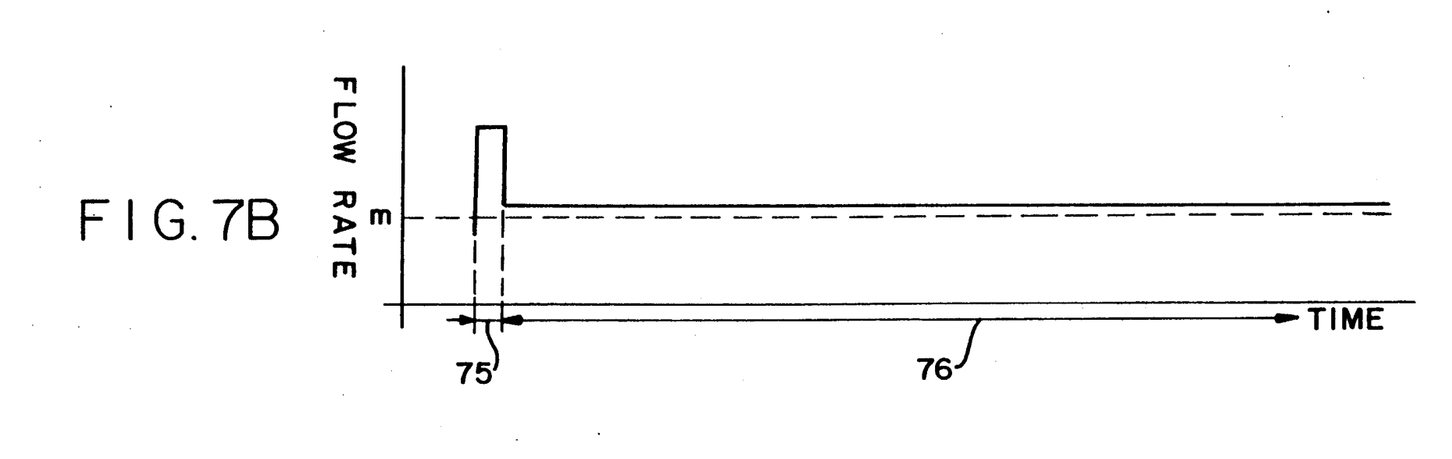
FIG. 7B is a graph of irrigant flow rate versus time in the angioscope irrigation system of FIG. 6.

FIGS. 7A and 7B illustrate several advantages of the present invention over irrigating techniques currently practiced in angioscopy. As FIG. 7A shows, the irrigation technique associated with the apparatus of FIG. 5 results in a continually changing flow rate of infusion. An assistant initially manually pressurizes saline bag 53 by means of hand bulb 55 during an interval 71. The initial flow rate quickly clears the visual field of blood and will maintain this clear field for a short time. However, as irrigant drains from bag 53, the pressure in the bag decreases. The fall in pressure causes a gradual decrease in flow rate during interval 72. At the end of that interval, the flow rate falls below a minimum flow rate needed to maintain a clear visual field and blood returns to the vessel, obscuring the operator's view. The assistant then manually repressurizes the bag during an interval 73, once again establishing sufficient flow for the greater portion of that interval and a subsequent falling rate interval 74.

FIG. 7B illustrates the results of using the apparatus depicted in FIG. 6. The operator first fully depresses footswitch 122 to activate the high flow mode to quickly infuse a bolus of irrigant during an interval 75 and fill the vessel under observation. Once the vessel is filled with sufficient irrigant to establish a desired visual field within the vessel, the operator, viewing through an eyepiece 103, then switches to the low flow mode by decreasing the force on footswitch 122. The rate of infusion in the low flow mode is preset to be just sufficient to keep the field clear during an indefinite interval 76. If the flow rate is incorrect, it can be adjusted during the procedure by means of buttons 135b on front panel 124 until the desired flow rate is established. As FIGS. 7A and 7B illustrate, substantially automated system according to the present invention offers reduced dependence on an assistant and a reduced volume of irrigant infused into the patient during the angioscopy procedure. These factors are critical to both the convenience and safety of angioscopy.

As will be apparent from the foregoing, the present invention provides the following advances over currently practiced irrigation techniques for angioscopy: (1) The operator has complete control over the start and stop of irrigant flow without the necessity of summoning an assistant for help. (2) The operator can precisely and adjustably preselect flow rates at which to infuse irrigant. (3) The preset flow rates are continuously displayed on the front panel of the pump unit. (4) The two modes of operation allow the operator to quickly fill the vessel and displace a column of blood, thereby clearing the field of view, and once the vessel is filled, the operator can easily switch to a lower infusion rate to sufficiently maintain the column of irrigant while he inspects the vessel interior. (5) The provision of an air bubble detection system prevents the inadvertent infusion of air into the patient. (6) The total amount of fluid infused into the patient is displayed on the front panel. (7) The pressure of infusion at the pump head is displayed on the front panel. (8) The irrigant is conveyed through the pump by means of a sterile, single-use tubing set and therefore does not come into direct contact with a non-sterile pump. (9) The design of the system minimizes the amount of irrigant required for angioscopy, thereby increasing the safety of the procedure.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An angioscope irrigation system comprising:
    an irrigation catheter for insertion into a blood vessel through a wall thereof for introducing an irrigation fluid into said vessel;
    a tubing set connected to said irrigation catheter comprising
        a) an inflow tube for receiving said irrigation fluid;
        b) an outflow tube for receiving said irrigation fluid from said inflow tube and transporting said irrigation fluid to said irrigation catheter;
        c) an air bubble detection means connected to said inflow tube for detecting an air bubble in said irrigation fluid being moved through said tubing set and for automatically deactivating an irrigation fluid drive means upon detection of an air bubble;
    said irrigation fluid drive means comprising a peristaltic pump in contact with said tubing set for moving said irrigation fluid; said fluid drive means having a first and second mode of operation for moving fluid through said tubing set at a plurality of different flow rates, said first mode producing a high pressure and flow rate to fill said blood vessel rapidly with irrigation fluid thereby displacing blood in the vessel with a bolus of irrigation fluid and said second mode following said first mode and producing a lower flow rate sufficient to keep said blood vessel clear for visual inspection;
    control means, operatively connected to said fluid drive means, whereby an operator can select said first and second mode of operation wherein said control means includes means for preselecting a volume of fluid to be delivered via said tubing set during said first mode of operation; and
    means for automatically deactivating said fluid drive means upon detection of an air bubble in said air bubble detection means.

2. The angioscope irrigation system set forth in claim 1 wherein said control means includes a first means for preselecting a first rate of fluid flow associated with said first mode and a second means for continuously varying a rate of fluid flow associated with said second mode.

3. The angioscope irrigation system set forth in claim 2 wherein said second means includes a manually actuatable control.

4. The angioscope irrigation system set forth in claim 3 wherein said manually actuatable control includes a footswitch.

5. The angioscope irrigation system set forth in claim 1, further comprising sensor means for monitoring fluid pressure in said tubing set.

6. The angioscope irrigation system set forth in claim 1, further comprising display means operatively connected to said irrigation fluid drive means for indicating a total amount of fluid pumped through said tubing set during an irrigation operation.

7. The angioscope irrigation system set forth in claim 1, further comprising display means operatively connected to said fluid drive means for indicating a rate of fluid flow through said tubing set.

8. The angioscope irrigation system set forth in claim 1, wherein said control means includes selection means having a manually actuatable control for presetting said first and second modes of operation so that each of said different flow rates has a respective predetermined value.

* * * * *